United States Patent
Yamane et al.

(10) Patent No.: US 7,235,673 B2
(45) Date of Patent: Jun. 26, 2007

(54) GLYCOLIDE PRODUCTION PROCESS, AND GLYCOLIC ACID OLIGOMER FOR GLYCOLIDE PRODUCTION

(75) Inventors: Kazuyuki Yamane, Fukushima (JP); Yukichika Kawakami, Fukushima (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 10/472,719

(22) PCT Filed: Apr. 10, 2002

(86) PCT No.: PCT/JP02/03570

§ 371 (c)(1),
(2), (4) Date: Sep. 19, 2003

(87) PCT Pub. No.: WO02/083661

PCT Pub. Date: Oct. 24, 2002

(65) Prior Publication Data

US 2004/0122240 A1 Jun. 24, 2004

(30) Foreign Application Priority Data

Apr. 12, 2001 (JP) .............................. 2001-113577

(51) Int. Cl.
*C07D 319/12* (2006.01)
*C08F 301/00* (2006.01)
(52) U.S. Cl. ..................... 549/274; 524/765; 524/766; 525/450
(58) Field of Classification Search ............... 549/274; 560/185, 198; 524/765, 766; 525/450

See application file for complete search history.

(56) References Cited

U.S. PATENT DOCUMENTS

| | | | |
|---|---|---|---|
| 2,668,162 A | | 2/1954 | Lowe |
| 2,999,033 A | * | 9/1961 | Bowman et al. ......... 106/273.1 |
| 4,727,163 A | | 2/1988 | Bellis |
| 4,835,293 A | | 5/1989 | Bhatia |
| 5,023,349 A | | 6/1991 | Bhatia |
| 5,830,991 A | | 11/1998 | Shiiki et al. |

FOREIGN PATENT DOCUMENTS

| | | |
|---|---|---|
| EP | 0789023 | 8/1997 |
| FR | 2692263 | 12/1993 |
| JP | 9-328481 | 12/1997 |
| JP | 11-116666 | 4/1999 |
| JP | 2002114775 | 4/2002 |

* cited by examiner

*Primary Examiner*—Bernard Dentz
(74) *Attorney, Agent, or Firm*—Dinsmore & Shohl LLP

(57) ABSTRACT

The invention relates to a glycolide production process wherein a depolymerization reaction system comprising a glycolic acid oligomer or a glycolic acid oligomer and a polar organic solvent is heated to depolymerize the glycolic acid oligomer into glycolide, the resulting glycolide or the glycolide and polar organic solvent are distilled out of the depolymerization reaction system, and the glycolide is recovered from distillates obtained by distillation. The glycolic acid oligomer or the glycolic acid oligomer and polar organic solvent are continuously or intermittently charged into the depolymerization reaction system, thereby carrying out depolymerization reactions continuously or repeatedly. During the depolymerization reactions, a compound having an alcoholic hydroxyl group is permitted to exist at a specific quantitative ratio in the depolymerization reaction system. The invention is also concerned with a glycolic acid oligomer for the production of glycolide, which is obtained by condensation of glycolic acid in the presence of the compound having an alcoholic hydroxyl group.

18 Claims, No Drawings

GLYCOLIDE PRODUCTION PROCESS, AND GLYCOLIC ACID OLIGOMER FOR GLYCOLIDE PRODUCTION

TECHNICAL FIELD

The present invention relates generally to a process for the production of glycolide that is a cyclic dimer ester of glycolic acid, and more particularly to a glycolide production process by depolymerization by heating of glycolic acid oligomers, which ensures the long-term stability of a depolymerization reaction system comprising a glycolic acid oligomer, so that the depolymerization reaction can be performed in a stable yet efficient manner even when the depolymerization reaction is carried out continuously or repeatedly.

The present invention is also concerned with a novel glycolic acid oligomer, which can reduce or substantially eliminate adverse influences ascribable to impurities contained in glycolic acid that is the raw material for glycolic acid oligomers, so that the depolymerization reaction can be carried out in a stable yet efficient fashion even when the depolymerization reaction is conducted continuously or repeatedly over an extended period of time.

BACKGROUND ART

Polyglycolic acid is a polyester formed by dehydration-polycondensation of glycolic acid (i.e., α-hydroxylacetic acid) and having the following formula:

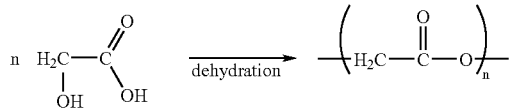

Polyglycolic acid is a biodegradable polymer that is hydrolyzed in vivo and, in natural environments, is metabolized and decomposed by microorganisms into water and carbonic acid gas. For this reason, the polyglycolic acid now attracts attention as environment-friendly polymer substitutes for medical materials or general-purpose. However, it is still difficult to obtain any polyglycolic acid having a high molecular weight by means of the dehydration-polycondensation of glycolic acid.

According to another polyglycolic acid production process so far known in the art, glycolide of the following formula, which is a cyclic dimer ester of glycolic acid is first synthesized.

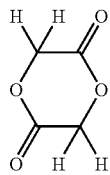

Then, this glycolide is subjected to ring-opening polymerization in the presence of a catalyst such as stannous octoate.

To produce polyglycolic acid (also called "polyglycolide") having a high molecular weight by the ring-opening polymerization of glycolide, it is required to use high-purity polyglycolide as the starting material. To use glycolide as the starting material to produce polyglycolic acid on an industrial scale, it is thus essential to economically feed such high-purity glycolide.

Glycolide is a cyclic ester compound having the structure wherein two water molecules are eliminated from two glyclolic acid molecules. Only by the esterification reaction of glycolic acid, however, any glycolide cannot be obtained because of the formation of glycolic acid oligomers. So far, various glycolide production processes have been proposed.

U.S. Pat. No. 2,668,162 discloses a process in which a glycolic acid oligomer is crushed into powders and heated at 270 to 285° C. under an ultra-high vacuum (12 to 15 Torr (1.6 to 2.0 kPa)) while the powders are fed to a reaction vessel in small portions (about 20 g/hour) for depolymerization, and the resultant glycolide-containing vapor is entrapped. This process, albeit being suitable for small-scale production, is found to have difficulty in large-scale production and so unsuitable for mass production. In addition, this process causes the oligomer to become heavy upon heating and so remain in the form of much residues in the reaction vessel, resulting in decreased glycolide yields and the need of cleaning off the residues. To add to this, the process makes glycolide (having a melting point of 82 to 83° C.) and byproducts likely to separate out in recovery lines, ending up with troubles such as line clogging.

U.S. Pat. No. 4,727,163 shows a glycolide production process wherein a polyether having good thermal stability is used as a substrate, a small amount of glycolic acid is then block copolymerized with the substrate to obtain a block copolymer, and the block copolymer is finally heated for depolymerization. However, this block copolymerization process is intractable and incurs some considerable production cost. In addition, the process makes glycolide and byproducts likely to separate out in recovery lines, leading to troubles such as line clogging.

U.S. Pat. Nos. 4,835,293 and 5,023,349 teach a process wherein an α-hydroxycarboxylic acid oligomer such as a polyglycolic acid oligomer is heated into a melt, and a cyclic dimer esters such as glycolide generated and vaporized out of the surface of the melt is entrained in an inert gas such as nitrogen gas and stripped in a low-boiling solvent such as acetone or ethyl acetate for recovery. With this process, it is still difficult to cut back on production costs, because of problems such as a slow formation rate of the cyclic dimer ester, possible formation of heavy materials in the melt, and the need for preheating for blowing a large amount of inert gas into the melt.

French Patent No. 2692263-A1 discloses a process for the production of a cyclic dimer ester wherein an oligomer of an α-hydroxycarboxylic acid or its ester or salt is added to a solvent with a catalyst added thereto, and then stirred in the presence of heat for catalytic decomposition. This process is carried out under normal or applied pressure, using a solvent suitable for entraining the cyclic dimer ester therein in a gaseous phase state. The gaseous phase is then condensed for the recovery of the cyclic dimer ester and solvent. The specification refers to only an example wherein a lactic acid oligomer is used as the raw feed and dodecane (having a boiling point of about 214° C.) is employed as the solvent. However, the results of follow-up experimentation made by the inventors under the same conditions as described in the example and using a glycolic acid oligomer and dodecane showed that heavy materials begin to form simultaneously with the start of the depolymerization reaction, the formation of glycolide stops at a point of time when a very slight amount of glycolide is formed, and much labor is needed for cleaning reaction residues because they are too viscous.

JP-A 09-328481 filed by the applicant of this application discloses a process comprising the steps of heating and depolymerizing an α-hydroxycarboxylic acid oligomer such as a glycolic acid oligomer in a polar organic solvent having a high boiling point, and distilling out the resultant cyclic dimer ester such as glycolide together with the polar organic solvent, and removing the cyclic dimer ester from the distillates.

The results of the inventors' subsequent investigation have showed that if a polyalkylene glycol ether having satisfactory thermal stability is used as the polar organic solvent in this process, cost reductions can then be achieved by recycling the solvent.

When a glycolic acid oligomer synthesized with a commercially available industrial-grade aqueous solution of glycolic acid is depolymerized in a high-boiling polar organic solvent, however, it has been found that the depolymerization reaction system becomes gradually unstable and so the formation rate of glycolide becomes low. To achieve efficient mass-production of glycolide by the aforesaid process, the depolymerization reaction should preferably be carried out continuously or repeatedly in the same reaction vessel.

That is, the depolymerization reaction system comprising a glycolic acid oligomer and a polar organic solvent is heated to depolymerize the glycolic acid oligomer into glycolide, and the resulting glycolide is distilled together with the polar organic solvent out of the depolymerization reaction system. It is here noted that if the solution remaining in the depolymerization reaction system is continuously or intermittently replenished with a fresh glycolic acid oligomer and a fresh polar organic solvent, it is then possible to carry out the depolymerization reaction continuously or repeatedly over an extended period.

As the depolymerization reaction takes place continuously or repeatedly within the same reaction vessel, however, the formation rate of glycolide decreases gradually, and the depolymerization reaction system becomes viscous with a buildup of heavier materials, resulting in a possibility that the system may boil suddenly. To be more specific, when the depolymerization reaction is repeated at least ten times within the same reaction vessel, it is found that there is a noticeable drop of the distillation rate of glycolide.

The inventors have made further studies to elucidate the cause of this problem. As a result of hydrolysis under alkaline conditions of a glycolic acid oligomer synthesized using a commercially available industrial-grade aqueous solution of glycolic acid, it has thus been found that such a glycolic acid oligomer contains, in addition to glycolic acid, organic acids such as diglycolic acid and methoxy acetic acid. Although depending on how to produce glycolic acid, oxalic acid may also be detected.

When the depolymerization reaction is carried out continuously or repeatedly while this system Is replenished with a fresh glycolic acid oligomer and a fresh polar organic solvent, these organic acids are built up in the depolymerization reaction system because of their relatively high boiling points. The accumulation of the organic acids within the depolymerization reaction system has now been found to have adverse influences on the depolymerization reaction.

The instability of the depolymerization reaction system and the decreased formation rate of glycolide due to such organic acid impurities may possibly be prevented by using an aqueous solution of high-purity glycolic acid or purifying an industrial-grade aqueous solution of glycolic acid thereby reducing the organic acid impurity content thereof. However, the glycolic acid purification step costs much, and so goes against glycolide production cost reductions and eventually provides an obstacle to versatile applications of polyglycolic acid.

In addition, even with a glycolic acid oligomer synthesized using an aqueous solution of high-purity glycolic acid or a purified aqueous solution of glycolic acid, the accumulation of slight amounts of organic acid impurities causes the depolymerization reaction to become gradually instable and the formation rate of glycolide to decrease, when the depolymerization reaction is carried out continuously or repetitively over an extended period. Thus, further improvements are still needed so as to achieve stable, efficient, low-cost production of high-purity glycolide on an industrial scale.

DISCLOSURE OF THE INVENTION

One object of the present invention is to provide a process for producing glycolide by depolymerization by heating of glycolic acid oligomers wherein, by imparting long-term stability to a depolymerization reaction system comprising a glycolic acid oligomer, depolymerization reactions can be run stably yet with efficiency, even when the depolymerization reactions are carried out over an extended period.

Another object of the present invention is to provide an unheard-of glycolic acid oligomer capable of reducing or substantially eliminating adverse influences ascribable to impurities contained in glycolic acid that is the raw material for glycolic acid oligomers, so that de-polymerization reactions can be carried out stably yet with efficiency, even when they are run continuously or repeatedly over an extended period.

As a consequent of intensive studies made to accomplish the aforesaid objects, the inventors have now found that if, in a glycolide production process comprising a step of the depolymerization by heating of a glycolic acid oligomer, a compound (A) having an alcoholic hydroxyl group is allowed to exist in a depolymerization reaction system during a depolymerization reaction, provided that the amount of the compound (A) in the depolymerization reaction system is controlled such that the alcoholic hydroxyl group amount of the compound (A) is kept at 0.5 equivalent or greater with respect to the total carboxyl group amount of an organic acid (B) comprising diglycolic acid, methoxy acetic acid and oxalic acid formed upon hydrolysis of the depolymerization reaction system under alkaline conditions, it is then possible to stabilize the de polymerization reaction system over an extended period.

According to the process wherein the compound having an alcoholic hydroxyl group is permitted to exist, glycolide can be obtained stably yet with efficiency, even when the depolymerization reaction is carried out continuously or repeatedly within the same reaction vessel. According to the production process of the invention, it is thus possible to achieve economical mass production of glycolide on an industrial scale.

It has also been found that by using as the raw material a glycolic acid oligomer that is obtained by the condensation of glycolic acid in the presence of the compound (A) having an alcoholic hydroxyl group and a boiling point of 190° C. or higher as well, it is possible to obtain glycolide stably yet with efficiency, even when the depolymerization reaction is carried out continuously or repeatedly within the same reaction vessel. These findings have underlain the present invention.

Thus, the present invention provides a glycolide production process including a step of depolymerization by heating of a glycolic acid oligomer, characterized in that:

a depolymerization reaction is carried out through the following steps (i) to (iv):

step (i) of heating a depolymerization reaction system comprising a glycolic acid oligomer or a glycolic acid oligomer plus a polar organic solvent to depolymerize the glycolic acid oligomer into glycolide, step (ii) of distilling the glycolide formed by depolymerization or the glycolide and polar organic solvent out of the depolymerization reaction system, step (iii) of recovering the glycolide from distillates obtained by distillation, and step (iv) of charging the glycolic acid oligomer or the glycolic acid oligomer and polar organic solvent continuously or intermittently into the depolymerization reaction system, in which:

(v) during the depolymerization reaction, a compound (A) having an alcoholic hydroxyl group is permitted to exist in the depolymerization reaction system, provided that the amount of the compound (A) in the depolymerization reaction system is controlled such that the alcoholic hydroxyl group amount of said compound (A) is kept at 0.5 equivalent or greater with respect to the total carboxyl group amount of an organic acid (B) comprising diglycolic acid, methoxy acetic acid and oxalic acid formed upon hydrolysis of the depolymerization reaction system under alkaline conditions.

The present invention also provides a glycolic acid oligomer for the production of glycolide, which is obtained by the condensation of glycolic acid in the presence of the compound (A) having an alcoholic hydroxyl group and a boiling point of 190° C. or higher as well.

BEST MODE FOR CARRYING OUT THE INVENTION

1. Depolymerization Reaction

By way of example but not by way of limitation, the depolymerization method usable herein includes melt depolymerization as set forth typically in U.S. Pat. No. 2,668,162, solution depolymerization as set forth typically in U.S. Pat. No. 5,830,991 and JP-A 09-328481, and solid-phase depolymerization as set forth typically in JP-A 11-116666.

Thus, the "depolymerization reaction system" used herein is generally broken down into a system composed substantially of a glycolic acid oligomer alone, and a system comprising a glycolic acid oligomer and a polar organic solvent, depending on the depolymerization method used.

Heating of the depolymerization reaction system composed substantially of a glycolic acid oligomer alone causes the glycolide resulting from the depolymerization reaction to sublimate or evaporate. It is here noted that the discharge of the sublimated or evaporated glycolide out of the depolymerization reaction system is also referred to as "distillation". Heating is carried out under normal pressure or reduced pressure. It is also possible to blow an inert gas into the depolymerization reaction system, thereby carrying the resulting glycolide therewith out of the system.

As the depolymerization reaction system comprising a mixture of a glycolic acid oligomer and a polar organic solvent is heated, the glycolide resulting form the depolymerization reaction and the polar organic solvent are co-distilled out. By separating the glycolide from distillates, the glycolide may be recovered. In this case, too, the depolymerization reaction is carried out by heating the depolymerization reaction system under normal pressure or reduced pressure.

Preferably in the present invention, the solution depolymerization process for depolymerizing the glycolic acid oligomer in a solution-phase state should be used in view of prevention of the glycolic acid oligomer used as the raw material from turning into heavier material and glycolide production efficiency.

A preferable solution depolymerization process used herein includes the following steps (i), (ii) and (iii). At step (i) the depolymerization reaction system comprising a glycolic acid oligomer and a polar organic solvent is heated for the depolymerization of the glycolic acid oligomer into glycolide, at step (ii) the glycolide resulting from the depolymerization and the polar organic solvent are co-distilled out of the depolymerization reaction system, and at step (iii) the glycolide is separated and recovered from the distillates obtained by distillation.

Preferably at the aforesaid step (i), a depolymerization reaction system composed of a mixture comprising a glycolic acid oligomer and an organic solvent having a boiling point of 230 to 450° C. is heated under normal pressure or reduced pressure until the proportion of a glycolic acid oligomer melt phase remaining in the mixture is reduced down to 0.5 or less. In this state, heating is continued for the depolymerization of the glycolic acid oligomer into glycolide. This is because the depolymerization reaction can be carried out with efficiency. The polar organic solvent should preferably have a molecular weight in the range of 150 to 450. A particularly preferred polar organic solvent is a polyalkylene glycol diether.

When a mixture comprising a glycolic acid oligomer and a polar organic solvent is used for the depolymerization reaction system, the mixture is heated to a temperature of usually 230° C. or higher under normal pressure or reduced pressure so that the whole, or a substantial, portion of the glycolic acid oligomer is dissolved in the polar organic solvent. More exactly, the glycolic acid oligomer is dissolved in the polar organic solvent until the proportion of the glycolic acid oligomer melt phase in the mixture is reduced down to 0.5 or lower.

Where a substantial portion of the glycolic acid oligomer is not dissolved in the polar organic solvent, the proportion of the oligomer melt phase becomes too high to distill out glycolide. In addition, heavy material-formation reactions are likely to occur in the oligomer melt phase. By depolymerizing the glycolic acid oligomer in a solution state, the formation rate of glycolide generated and vaporized out of the surface of the oligomer can be much more increased. In this regard, it is preferable that upon the mixture heated to a temperature at which depolymerization occurs, the glycolic acid oligomer is already completely dissolved in the polar organic solvent; the melt phase is kept against any phase separation.

It is here noted that the term "proportion of the glycolic acid oligomer melt phase" remaining in the mixture refers to the volume ratio of the oligomer melt phase formed in an actually used polar organic solvent with the proviso that the volume of the oligomer melt phase formed in a solvent such as liquid paraffin, in which the glycolic acid oligomer is substantially insoluble, is 1.

When the sole use of the polar organic solvent is found to make the solubility of the glycolic acid oligomer insufficient, it may be enhanced by conducting heating in the presence of the compound (A) having an alcoholic hydroxyl group.

Heating is carried out under normal pressure or reduced pressure; however, it should preferably be done under a reduced pressure of about 0.1 to 90 kPa. Heating should desirously be performed in an inert atmosphere. The mixture is heated to at least 230° C., at which the depolymerization reaction of glycolic acid oligomer occurs. However, usually, the mixture is heated to temperatures in the range of 230 to 320° C., preferably 235 to 300° C., and more preferably 240 to 290° C.

By heating, the depolymerization of glycolic acid oligomer takes place, and the resulting glycolide is co-distilled out together with the polar organic solvent. Since the resultant glycolide is co-distilled out together with the organic solvent, it is possible to prevent any deposition of glycolide on the wall surfaces of a reaction vessel and lines, which may otherwise cause accumulation of glycolide. The distillates are then guided out of the depolymerization reaction system to recover glycolide therefrom. The distillates are cooled, if required, with a nonsolvent added thereto, so that glycolide is separated out and solidified. The separated-out glycolide is isolated from the mother liquor by means of filtration, centrifugal sedimentation, decantation, etc. If required, the isolated glycolide is washed or extracted with a nonsolvent such as cyclohexane or ether, and then recrystallized with ethyl acetate or the like. The glycolide may also be purified by distillation.

The mother liquor, from which glycolide has been isolated, may be recycled without any purification. Alternatively, the mother liquor may be filtered out and purified by treatment with activated carbon, etc. for recycling purposes. Still alternatively, the mother liquor may be purified by redistillation for recycling purposes.

As glycolide is co-distilled out of the depolymerization reaction system together with the polar organic solvent, there is a decrease in the volume of the depolymerization reaction system. If fresh amounts of the glycolic acid oligomer and polar organic solvent—that make up for the amount of distillates—are additionally fed to the reaction system, it is then possible to carry out the depolymerization reaction in a continuous or repeated fashion over an extended period of time. According to the production process of the invention, the depolymerization reaction can be carried out in a stable manner, and so such a process can be used, thereby making striking improvements in production efficiency and cutting back on cost.

More specifically according to the invention, a mixture containing a glycolic acid oligomer and a polar organic solvent is charged into a reaction vessel to start the depolymerization reaction. With the progress of the depolymerization reaction, the resulting glycolide and polar organic solvent are co-distilled out of the depolymerization reaction system. If fresh amounts of the glycolic acid oligomer and polar organic solvent are added to the reaction solution remaining in the reaction vessel, the depolymerization reaction can then be carried out in a repetitive manner. Alternatively, the depolymerization reaction may be continuously carried out while the fresh amounts of the glycolic acid oligomer and polar organic solvent are supplied during the depolymerization reaction. The glycolic acid oligomer and polar organic solvent may be supplied into the depolymerization reaction system in a continuous or intermittent fashion, or in a combined continuous and intermittent fashion. It is here noted that the reaction solution remaining in the reaction vessel may be wholly or partly used.

In the present invention, the depolymerization reaction is carried out in a continuous or repetitive manner while the glycolic acid oligomer or the glycolic acid oligomer plus polar organic solvent is continuously or intermittently supplied into the depolymerization reaction system, and the depolymerization is effected in the state where the predetermined amount of the compound having an alcoholic hydroxyl group is always present in the depolymerization reaction system.

In order to carry out the depolymerization reaction within the same reaction vessel in a continuous or repetitive fashion, it is necessary that fresh amounts of the glycolic acid oligomer or the glycolic acid oligomer plus polar organic solvent be supplied continuously or intermittently into the depolymerization reaction system. Consequently, organic acid impurities are gradually built up within the depolymerization reaction system. In the present invention, the compound having an alcoholic hydroxyl group is allowed to be constantly present in the depolymerization reaction system in an amount corresponding to the amount of the thus built up organic acid impurities.

The amount of the compound (A) having an alcoholic hydroxyl group, which is permitted to exist in the depolymerization reaction system, is such that the alcoholic hydroxyl group amount is at least 0.5 equivalent, preferably at least 0.9 equivalent, and more preferably at least 1 equivalent with respect to the total carboxyl group amount of the organic acid (B) comprising diglycolic acid, methoxy acetic acid and oxalic acid formed upon hydrolysis of the depolymerization reaction system under alkaline conditions.

When the amount of the compound (A) having an alcoholic hydroxyl group, which is present in the depolymerization reaction system, is too small or when the alcoholic hydroxyl group amount of the compound (A) relative to the total carboxyl group amount of the organic acid (B) is less than 0.5 equivalent, it is difficult to control decreases in the formation rate of glycolide. When the amount of the compound (A) having an alcoholic hydroxyl group is too large, it is often likely that the depolymerization reaction system may be diluted, resulting in depolymerization reaction efficiency drops. In most cases, the depolymerization reaction system may be stabilized by keeping the alcoholic hydroxyl group amount of the compound (A) relative to the total carboxyl group amount of the organic acid (B) in the range of 0.5 to 1.5 equivalents. It is noted, however, that when the compound (A) having an alcoholic hydroxyl group takes another role of a solubilizer for improving the solubility of the glycolic acid oligomer in the polar organic solvent, it may be allowed to exist in the depolymerization reaction system in an amount of up to 100 parts by weight, and more preferably up to 50 parts by weight per 100 parts by weight of the glycolic acid oligomer.

By permitting the compound having an alcoholic hydroxyl group to exist within the depolymerization reaction system at a proportion of predetermined or larger equivalents relative to the carboxyl group amount of organic acid impurities, the depolymerization reaction system is so stabilized that any decrease in the formation rate of glycolide can be reduced. Any detailed reason for this has yet to be clarified. As the depolymerization reaction takes place continuously or repetitively, there is an increase in the amount of organic acid impurities accumulated in the depolymerization reaction system. When the ratio (b/a) between the terminal carboxyl group amount (b) of the organic acid impurities present in the depolymerization reaction system and the alcoholic hydroxyl group amount (a) is shifted to an increasing value, a condensation reaction competitive with the depolymerization reaction tends to occur. This is believed to lead to a decrease in the formation rate of glycolide. The compound (A) having an alcoholic hydroxyl group would react or otherwise combine chemically with the organic acid impurities, thereby reducing such a decrease.

How to add the compound (A) having an alcoholic hydroxyl group into the depolymerization reaction system is not particularly critical. For instance, the necessary amount of the compound (A) having an alcoholic hydroxyl group may be supplied to a reaction vessel simultaneously with, or before or after, the feed of the starting glycolic acid oligomer thereto. Alternatively, if the depolymerization reaction is carried out with the continuous or intermittent addition of the starting glycolic acid oligomer while an excess amount of the compound (A) having an alcoholic hydroxyl group has been added into the reaction vessel, it is then possible to add the compound (A) having an alcoholic hydroxyl group continuously or intermittently into the depolymerization reaction system before the total carboxyl group amount of the organic acid impurities in the depolymerization reaction system reaches the predetermined or greater equivalent weight with respect to the alcoholic hydroxyl group amount of the originally added compound (A) having an alcoholic hydroxyl group.

Where the depolymerization reaction is carried out repeatedly within the same reaction vessel, it is acceptable that when the fresh amounts of the glycolic acid oligomer or the glycolic acid oligomer plus polar organic solvent are supplied, the necessary amount of the compound (A) having an alcoholic hydroxyl group is added or a batch of the compound (A) is added upon the number of repetition of the depolymerization reaction reaching a constant or greater.

With the solution depolymerization process, the necessary amount of the compound having an alcoholic hydroxyl group may be added in the form of a solution wherein the glycolic acid oligomer and the predetermined amount of the compound having an alcoholic hydroxyl group are dissolved in the polar organic solvent. The amount of the compound (having an alcoholic hydroxyl group) used may be such that after the addition of said compound, the alcoholic hydroxyl group amount is at a predetermined or greater equivalent ratio (0.5 equivalent or more) with respect to the total carboxyl group amount of the organic acid impurities in the de polymerization reaction system. Practically, however, it is preferable to previously measure the total carboxyl group amount of the organic acid impurities contained in the starting glycolic acid oligomer. More exactly, the amount of the compound having an alcoholic hydroxyl group should be controlled in such a way that the rate of the alcoholic hydroxyl group amount with respect to that total carboxyl group amount is kept in the range of at least 0.5 equivalents, and preferably at 1.0 equivalents. At an equivalent ratio of less than 0.5, the alcoholic hydroxyl group amount in the depolymerization reaction system decreases and so the effect of the compound on the reduction of a decrease in the formation rate of glycolide does hardly manifest itself.

Instead of adding the compound (A) having an alcoholic hydroxyl group directly into the depolymerization reaction system, it is herein also possible to use as the starting glycolic acid oligomer a glycolic acid oligomer that is obtained by the condensation of glycolic acid in the presence of the compound (A) having an alcoholic hydroxyl group and a boiling point of at least 190° C. as well. By use of such a glycolic acid oligomer, the compound having an alcoholic acid, present in the depolymerization reaction system, may be kept in the predetermined quantitative range. Using as the raw material a glycolic acid oligomer that is obtained by co-condensation with the compound having an alcoholic hydroxyl group is preferable, because any separate addition of the compound having an alcoholic hydroxyl group is not always needed and so the depolymerization reaction operation is simplified.

Such a glycolic acid oligomer may be prepared by the co-condensation of glycolic acid in the presence of the compound (A) having an alcoholic hydroxyl group and under ordinarily available condensation conditions. In the co-condensates, the compound having an alcoholic hydroxyl group exists by itself or, alternatively, it exists in the glycolic acid oligomer, with a structure esterified by co-condensation with glycolic acid, diglycolic acid, methoxy acetic acid or oxalic acid. This would in turn reduce the actions of organic acid impurities.

Referring here to the amount of the compound (A) having an alcoholic hydroxyl group, which is allowed to coexist upon the condensation of glycolic acid, the alcoholic hydroxyl group amount should preferably be in the range of 0.5 to 1.5 equivalents with respect to the carboxyl group amount of the organic acid (B) comprising diglycolic acid, methoxy acetic acid and oxalic acid formed upon the hydrolysis under alkaline conditions of the glycolic acid oligomer obtained by condensation. When a glycolic acid oligomer obtained by the condensation of glycolic acid while the amount of the coexisting alcoholic hydroxyl group is set at greater than 1.5 equivalents with respect to the total carboxyl group amount of the organic acid impurities is added as the raw material, it is acceptable to dilute that compound (A) with a glycolic acid oligomer not subjected to condensation, thereby controlling the equivalent ratio of the alcoholic hydroxyl group in the aforesaid range.

Referring then to the amount of the compound (A) having an alcoholic hydroxyl group, which is permitted to coexist upon the condensation of glycolic acid, the alcoholic hydroxyl group amount should be in the range of preferably 0.5 to 1.5 equivalents, more preferably 0.8 to 1.2 equivalents, and even more preferably 0.9 to 1.1 equivalents with respect to the total carboxyl group amount of the organic acid (B) comprising diglycolic acid, methoxy acetic acid and oxalic acid formed upon the hydrolysis under alkaline conditions of the glycolic acid oligomer produced. The total carboxyl group amount of the organic acid (B) comprising diglycolic acid, methoxy acetic acid and oxalic acid formed upon the hydrolysis under alkaline conditions of the glycolic acid oligomer may here be considered substantially equal to the total carboxyl group amount of the organic acids contained in the starting glycolic acid.

2. Glycolic Acid Oligomer

Glycolic acid oligomers used herein may be synthesized by the condensation of glycolic acid that may be in the form of ester (e.g., lower alkyl esters) or salt (e.g., sodium salt).

Glycolic acid (inclusive of its ester or salt) is heated to at a temperature of usually 100 to 250° C., and preferably 140 to 230° C. under reduced or applied pressure and, if required, in the presence of a condensation catalyst or an ester exchange catalyst, so that a condensation reaction or an ester exchange reaction is carried out until distillation of low-molecular-weight materials such as water and alcohol is not substantially found. After the completion of the condensation reaction or ester exchange reaction, the resulting glycolic acid oligomer may be used immediately as the raw material in the present invention. If the resulting glycolic acid oligomer discharged out of the reaction system is washed with a non-solvent such as benzene or toluene, unreacted or low-molecular-weight materials, the catalyst or the like can then be removed therefrom. The glycolic acid oligomer used may be in a ring or straight-chain form, and the degree of polymerization is not particularly critical. In consideration of glycolide yields upon the depolymerization reaction, however, the glycolic acid oligomer used should have a melting point (Tm) of usually 140° C. or higher, preferably 160° C. or higher, and more preferably 180° C. or higher. The "Tm" used herein is understood to mean a melting point of a sample as detected with a differential scanning calorimeter (DSC) while the sample is heated at a heating rate of 10° C./minute in an inert gas atmosphere.

As already explained, the glycolic acid oligomer obtained by the condensation of commercially available glycolic acids includes, in addition to glycolic acid as a monomer unit, slight amounts of impure components, for instance, diglycolic acid, methoxy acetic acid, oxalic acid and so on. Of these impurities, organic acid impurities have relatively high boiling points. The organic acid impurities, even when contained in slight amounts, build up in the depolymerization reaction system as the de-polymerization reaction proceeds continuously or repetitively with the successive addition of the starting glycolic acid oligomer into the depolymerization reaction system, and consequently have adverse influences on the depolymerization reaction.

By the coexistence of the compound (A) having an alcoholic hydroxyl group according to the production process of the invention, the adverse influences of these organic acid impurities can be strikingly reduced or substantially eliminated. For this reason, no particular limitation is imposed on the glycolic acid oligomer used; for instance, it is possible to use inexpensive glycolic acid oligomers that are obtained by the dehydration-condensation of commercially available, industrial-grade aqueous glycolic acid solutions.

In glycolic acid oligomers obtained by conventional dehydration-condensation processes of commercially available, industrial-grade glycolic acids, there are organic acids comprising diglycolic acid, methoxy acetic acid and oxalic acid formed upon their complete hydrolysis under alkaline conditions, the total carboxyl group amount of which is usually at least 0.5 molt with respect to the glycolic acid. Still, the present invention makes it possible to use glycolic acid oligomers that contain a large amount of carboxyl groups resulting from such organic acid impurities.

A glycolic acid oligomer obtained by the condensation of glycolic acid in the presence of the compound having an alcoholic hydroxyl group and a boiling point of 190° C. or higher as well may be prepared by condensation under the production conditions for glycolic acid oligomers and in the presence of the predetermined amount of the compound having an alcoholic hydroxyl group.

3. Compound Having an Alcoholic Hydroxyl Group

The compound (A) having an alcoholic hydroxyl group, used in the present invention, should be permitted to exist in the depolymerization reaction system during the depolymerization reaction. Acid impurities or diglycolic acid, methoxy acetic acid and oxalic acid have all relatively high boiling points, and so are hardly removed out of the depolymerization reaction system by distillation under de-polymerization reaction conditions. It is thus preferable that the compound (A) having an alcoholic hydroxyl group, too, be hardly removed out of the system by distillation.

Specific examples of such a compound (A) having an alcoholic hydroxyl group are mono-, di- or poly-hydric alcohols (inclusive of their partially esterified or etherified products), phenols, etc. In particular, the alcohols are the most effective compounds having an alcoholic hydroxyl group; however, the most preference is given to polyhydric alcohols having at least two alcoholic hydroxyl groups per molecule. Even some low-molecular-weight polyhydric alcohols are more effective in small amounts than monohydric alcohols because of their merit of being hardly distilled out of the depolymerization reaction system. The compound (A) should have a boiling point of preferably at least 190° C., and more preferably at least 195° C.

Where the compound (A) having an alcoholic hydroxyl group is distilled out of the depolymerization reaction system, it is preferable to make up for losses by distillation.

Among the compounds (A) having an alcoholic hydroxyl group, preference is given to alkylene diols (p=1) or polyalkylene glycols (p≧2) and polyalkylene glycol monoethers having the following formulae (1) and (2), respectively, as well as tri- or poly-hydric alcohols such as glycerin, higher alcohols such as tridecanol, etc.

(1)

Here $R^1$ is a methylene group or a straight-chain or branched-chain alkylene group having 2 to 10 carbon atoms and p is an integer of 1 or greater provided that when p is an integer of 2 or greater, a plurality of $R^1$s may be identical with or different from each other.

(2)

Here $R^2$ is a methylene group or a straight-chain or branched-chain alkylene group having 2 to 10 carbon atoms, $X^1$ is a hydrocaron group and q is an integer of 1 or greater provided that when q is an integer of 2 or greater, a plurality of $R^2$s may be identical with or different from each other. Among these, preference is given to alkylene diols, polyalkylene glycols and polyalkylene glycol monoethers.

The alkylene diol (i.e., alkylene glycol) used herein, for instance, includes ethylene glycol, propylene glycol, butylene glycol, hexanediol, hexylene glycol, hexamethylene glycol and decanediol, among which ethylene glycol is preferred.

The polyalkylene glycol usable herein, for instance, includes polyethylene glycol, polypropylene glycol and polybutylene glycol.

The polyalkylene glycol monoether usable herein, for instance, includes polyethylene glycol monoalkyl ethers such as polyethylene glycol monopropyl ether, polyethylene glycol monobutyl ether, polyethylene glycol monohexyl ether, polyethylene glycol monooctyl ether, polyethylene glycol monodecyl ether and polyethylene glycol monolauryl ether, and polypropylene glycol monoalkyl ethers or polybutylene glycol monoalkyl ethers wherein the ethyleneoxy groups in the aforesaid compounds are substituted by propyleneoxy or butyleneoxy groups.

These compounds (A) having an alcoholic hydroxyl group may be used alone or in combination of two or more. The compounds (A) may also be used in combination with a glycolic acid oligomer obtained by co-condensation with a compound having an alcoholic hydroxyl group.

4. Polar Organic Solvent

When the depolymerization reaction is carried out by the solution depolymerization process, the polar organic solvent is used. The polar organic solvent is not only used as a solvent for the depolymerization reaction but is also co-distilled out together with the resulting glycolide so that the glycolide can be discharged out of the depolymerization reaction system. The polar organic solvent should preferably have a boiling point of 230 to 450° C. and a molecular weight in the range of 150 to 450.

When a polar organic solvent having too low a boiling point is used, no high depolymerization reaction temperature can be set so that the rate of formation of glycolide becomes low. When a polar organic solvent having too high a boiling point, on the other hand, the organic solvent is hardly distilled out upon the depolymerization reaction, and so the co-distillation of the polar organic solvent and the glycolide formed by depolymerization becomes difficult. The boiling point of the polar organic solvent used should be in the range of preferably 235 to 450° C., more preferably 260 to 430° C., and most preferably 280 to 420° C.

When the molecular weight of the polar organic solvent used deviates from the aforesaid range, the co-distillation of the polar organic solvent and glycolide becomes difficult. The molecular weight of the polar organic solvent used should be in the range of preferably 180 to 420, and more preferably 200 to 400.

The polar organic solvent, for instance, includes aromatic dicarboxylic acid diesters, aliphatic dicarboxylic acid diesters, and polyalkylene glycol diethers. The aromatic dicarboxylic diester used herein, for instance, includes phthallic esters such as dibutyl phthalate, dioctyl phthalate, dibenzyl phthalate and benzylbutyl phthalate and benzoic esters such as benzyl benzoate.

The aliphatic dicarboxylic diester used herein, for instance, includes adipic esters such as octyl adipate and sebacic esters such as dibutyl sebacate.

The polyalkylene glycol diether has the following formula (3):

$$X^2O-(R^3-O)_r-Y \quad (3)$$

Here $R^3$ is a methylene group or a branched-chain or straight-chain alkylene group having 2 to 8 carbon atoms, $X^2$ and Y are each a hydrocarbon group, and r is an integer of 1 or greater provided that when r is an integer of 2 or greater, a plurality of $R^3$s may be identical with or different from each other.

Exemplary such polyalkylene glycol diethers are polyethylene glycol dialkyl ethers such as diethylene glycol dibutyl ether, diethylene glycol dihexyl ether, diethylene glycol dioctyl ether, triethylene glycol dimethyl ether, triethylene glycol diethylene ether, triethylene glycol dipropyl ether, triethylene glycol dibutyl ether, triethylene glycol dihexyl ether, triethylene glycol dioctyl ether, tetraethylene glycol dimethyl ether, tetraethylene glycol diethyl ether, tetraethylene glycol dipropyl ether, tetraethylene glycol dibutyl ether, tetraethylene glycol dihyexyl ether, tetraethylene glycol dioctyl ether, diethylene glycol butylhexyl ether, diethylene glycol butyloctyl ether, diethylene glycol hexyloctyl ether, triethylene glycol butylhexyl ether, triethylene glycol butyloctyl ether, triethylene glycol hexyloctyl ether, tetraethylene glycol butylhexyl ether, tetraethylene glycol butyloctyl ether and tetraethylene glycol hexyloctyl ether as well as polyalkylene glycol dialkyl ethers wherein the ethyleneoxy groups in these compounds are substituted by propyleneoxy or butyleneoxy groups, e.g., polypropylene glycol dialkyl ethers or polybutylene glycol dialkyl ethers; polyethylene glycol alkylaryl ethers such as diethylene glycol butylphenyl ether, diethylene glycol hexylphenyl ether, diethylene glycol octylphenyl ether, triethylene glycol butylphenyl ether, triethylene glycol hexylphenyl ether, triethylene glycol octylphenyl ether, tetraethylene glycol butylphenyl ether, tetraethylene glycol hexylphenyl ether and tetraethylene glycol octylphenyl ether, polyethylene glycol alkylaryl ethers wherein the hydrogen groups in the phenyl groups in these compounds are substituted by an alkyl group, an alkoxy group or a halogen atom, and polyalkylene glycol alkylaryl ethers such as polypropylene glycol alkylaryl ethers or polybutylene glycol alkylaryl ethers containing propyleneoxy or butyleneoxy groups instead of the ethyleneoxy groups in these compounds; polyethylene glycol diaryl ethers such as diethylene glycol diphenyl ether, triethylene glycol diphenyl ether, tetraethylene glycol diphenyl ether, polyethylene glycol diaryl ethers wherein the phenyl groups in these compounds are substituted by an alkyl group, an alkoxy group, a halogen atom, etc., and polyalkylene glycol diaryl ethers such as polypropylene glycol diaryl ethers or polybutylene glycol diaryl ethers containing propyleneoxy or butyleneoxy groups instead of the ethyleneoxy groups in these compounds.

These polar organic solvents are used in an amount of, based on a mass basis, usually 0.3 to 50 times, preferably 0.5 to 20 times and more preferably 1 to 10 times as large as the glycolic acid oligomer.

EXAMPLES

By way of example but not by way of limitation, the present invention is now explained more specifically with reference to synthesis examples, inventive examples and a comparative example.

(1) Quantitative Determination Of Diglycolic Acid, Methoxy Acetate, and Oxalic Acid A sample (5.8 grams) was placed in a 200-ml beaker with the addition of 4 grams of NaOH and 40 grams of distilled water thereto, wherein perfect hydrolysis was carried out at 40° C. under agitation for 12 to 48 hours. After regulated by sulfuric acid to pH 4.7, the resulting hydrolysis solution was provided with distilled water in such a way as to give a total amount of 80 grams. This testing solution (2 grams) was diluted with distilled water to 50 ml, 2 μl of which were analyzed by high performance liquid chromatography (HPLC) under the following conditions.

The contents of glycolic acid, diglycolic acid, methoxy acetic acid and oxalic acid were found by the absolute calibration curve method on the basis of calibration curves determined ahead from the respective standard substances.

The contents of diglycolic acid, methoxy acetic acid and oxalic acid are all given by moles in a solution state, and in terms of molt as well.

Analytical Conditions for HPLC
Apparatus: L-6200, Hitachi, Ltd.
Column: Intersil ODS-3V (5 μm), 250×4.6 mm I.D.
Flow Rate: 1.0 mL/min.
Eluate: Aqueous solution of 0.1 M ammonium dihydrogenphosphate+phosphoric acid
Oven Temperature: 40° C.
Detection Condition: UV 210 nm

Synthesis Example 1

Synthesis of Glycolic Acid Oligomer (a)

A 5-liter autoclave was charged with 3,500 grams of a commercially available 70% aqueous solution of glycolic acid (of the industrial grade, Du Pont). While stirred at normal pressure, the solution was heated from 170° C. up to 200° C. over 2 hours for a condensation reaction during which the formed water was distilled out. Then, the internal pressure of the autoclave was lowered to 5.0 kPa, at which the solution was heated at 200° C. for 2 hours to distill off low-boiling materials including unreacted matters, thereby preparing 1,700 grams of glycolic acid oligomer (a). The proportions of diglycolic acid, methoxy acetic acid and oxalic acid in the glycolic acid oligomer (a) were found through an analysis by hydrolysis under alkaline conditions to be 1.0 mol %, 0.5 mol % and 0 mol %, respectively, per mole of glycolic acid.

Synthesis Example 2

Synthesis of Glycolic Acid Oligomer (b)

As in synthesis example 1, 1,650 grams of glycolic acid oligomer (b) were obtained with the exception that the aqueous solution of glycolic acid was changed to 3,570 grams of a commercially available 70% aqueous solution of high-purity glycolic acid (of no industrial grade, Du Pont) with the addition thereto of 32 grams of oxalic acid having a molecular weight of 90. The proportions of diglycolic acid, methoxy acetic acid and oxalic acid in the glycolic acid oligomer (b) were found through an analysis by hydrolysis under alkaline conditions to be 0 mol %, 0 mol % and 1.25 mol %, respectively, per mole of glycolic acid.

Synthesis Example 3

Synthesis of Glycolic Acid Oligomer (c)

A 5-liter autoclave was charged with 3,500 grams of a commercially available 70% aqueous solution of glycolic acid (of the industrial grade, Du Pont) and 250 grams of lauryl triethylene glycol having a molecular weight of 318.5. While stirred at normal pressure, the solution was heated from 170° C. up to 200° C. over 2 hours for a condensation reaction during which the formed water was distilled out. Then, the internal pressure of the autoclave was lowered to 5.0 kPa, at which the solution was heated at 200° C. for 2 hours to distill off low-boiling materials including unreacted matters, thereby preparing 1,750 grams of glycolic acid oligomer (c). The proportions of diglycolic acid, methoxy acetic acid and oxalic acid in the glycolic acid oligomer (c) were found through an analysis by hydrolysis under alkaline conditions to be 1.0 mol %, 0.5 mol % and 0 mol %, respectively, per mole of glycolic acid.

This synthesis example 3 is tantamount to an example of the invention relating to the glycolide-producing glycolic acid oligomer that is obtained by the condensation of glycolic acid in the presence of the compound (A) having an alcoholic hydroxyl group and a boiling point of 190° C. or higher as well.

Synthesis Example 4

Synthesis of Polyalkylene Glycol Ether

Commercially available polyethylene glycol dimethyl ether #250 (made by Merck) was distilled to obtain tetraethylene glycol dimethyl ether having a polymerization degree of 4 (hereinafter abbreviated as TEGDME). The TEGDME was used as the polar organic solvent for the solution depolymerization process.

Example 1

A 500-ml flask was charged with 100 grams of glycolic acid oligomer (a) obtained in synthesis example 1, 200 grams of TEGDME acting as the polar organic solvent and 42 grams (corresponding to 0.28 mole of alcoholic hydroxyl group) of polyethylene glycol #300 having an average molecular weight of 300 and a boiling point of 410 to 470° C. (hereinafter referred to as PEG#300). The flask was heated up to 260° C. while the inside pressure was lowered to 8.0 kPa. Glycolic acid oligomer (a) was put in a dissolved state, with the proportion of its remaining melt phase being substantially zero. A solution distilled out of the depolymerization reaction system was cooled with ice water for entrapment.

After a five-hour reaction, the amount of the distilled-out solution was 210 grams. From this solution, 58 grams of glycolide and 150 grams of TEGDME were recovered. The distillation rate of glycolide was 11 to 12 grams/hour. With 60 grams of glycolic acid oligomer (a) and 150 grams of TEGDME added to the reaction solution remaining in the flask, the depolymerization reaction was carried out under the same conditions as mentioned above.

In this way, the depolymerization reaction was repetitively carried out with the addition of glycolic acid oligomer (a) in the weight corresponding to the amount of glycolide obtained in the distilled-out solution and TEGDME in the same amount as that of TEGDME in the distilled-out solution.

The depolymerization reaction was repeated ten times. The feed of glycolic acid oligomer (a) added up to 640 grams. At the time when the depolymerization was repeated ten times, the distillation rate of glycolide started to become low. More exactly, the distillation rate of glycolide decreased down to 8 to 9 grams/hour. Then, the 11th depolymerization reaction was carried out with the addition of 4 grams of PEG#300 to 60 grams of glycolic acid oligomer (a). Consequently, the distillation rate of glycolide again went back to the initial distillation rate of 11 to 12 grams/hour. Likewise, the 12th to 15th depolymerization reactions were successively carried out with the addition of 60 grams of glycolic acid oligomer (a), 4 grams of PEG#300 and 150 grams of TEGDME. Subsequently, the 16th to 20th depolymerization reactions were successively carried out with the addition of 60 grams of glycolic acid oligomer (a), 8.3 grams of lauryl triethylene glycol having a molecular weight of 318.5 and a boiling point of 450° C. or higher and 150 grams of TEGDME, whereupon the 21st to 25th depolymerization reactions were successively done with the addition of 60 grams of glycolic acid oligomer (a), 1.3 grams of ethylene glycol having a molecular weight of 62 and a boiling point of 197° C. and 150 grams of TEGDME. At the 11th through the 25th depolymerization reactions, the distillation rate of glycolide was kept stable at 11 to 12 grams/hour, indicating that the stable yet efficient depolymerization reactions could be carried out over an extended period.

Upon the completion of the 25th reaction, the feed of glycolic acid oligomer (a) added up to 1,540 grams. The depolymerization reaction system (the reaction solution remaining in the flask) was hydrolyzed under alkaline conditions to analyze the contents of diglycolic acid, methoxy acetic acid and oxalic acid present therein. As a result, the respective contents were found to be 0.26 mole, 0.13 mole and 0 mole. The amount of carboxyl groups in these organic acids totaled 0.65 mole. The amount of the compound having an alcoholic hydroxyl group, added at the initial stage and the subsequent stages, was 62 grams for PEG#300, 41.5 grams for lauryl triethylene glycol and 6.5 grams for ethylene glycol, and the amount of the respective alcoholic hydroxyl groups totaled 0.65 mole.

Example 2

A 500-ml flask was charged with 100 grams of glycolic acid oligomer (b) obtained in synthesis example 2, 200 grams of TEGDME acting as the polar organic solvent and 42 grams (corresponding to 0.28 mole of alcoholic hydroxyl group) of PEG#300 having an average molecular weight of 300 and a boiling point of 410 to 470° C. The flask was heated up to 260° C. while the inside pressure was lowered to 8.0 kPa. Glycolic acid oligomer (b) was put in a dissolved state. A solution distilled out of the depolymerization reaction system was cooled with ice water for entrapment.

After a five-hour reaction, the amount of the distilled-out solution was 208 grams. From this solution, 59 grams of glycolide and 149 grams of TEGDME were recovered. The distillation rate of glycolide was 11 to 12 grams/hour. With 60 grams of glycolic acid oligomer (b) and 150 grams of TEGDME added to the reaction solution remaining in the flask, the depolymerization reaction was carried out under the same conditions as mentioned above. In this way, the depolymerization reaction was repetitively carried out with the addition of glycolic acid oligomer (b) in the weight corresponding to the amount of glycolide obtained in the distilled-out solution and TEGDME in the same amount as that of TEGDME in the distilled-out solution. The depolymerization reaction was repeated ten times. The feed of glycolic acid oligomer (b) added up to 640 grams. At the 10th depolymerization reaction, the distillation rate of glycolide decreased down to 9 to 10 grams/hour. Then, the 11th depolymerization reaction was carried out with the addition of 4 grams of PEG#300 to 60 grams of glycolic acid oligomer (b). Consequently, the distillation rate of glycolide again went back to the initial distillation rate of 11 to 12 grams/hour. Likewise, the 12th to 25th depolymerization reactions were successively carried out with the addition of 60 grams of glycolic acid oligomer (b), 4 grams of PEG#300 and 150 grams of TEGDME. At the 11th through the 25th depolymerization reactions, the distillation rate of glycolide was kept stable at 11 to 12 grams/hour, indicating that the stable yet efficient depolymerization reactions could be carried out over an extended period.

Upon the completion of the 25th reaction, the feed of glycolic acid oligomer added up to 1,540 grams. The depolymerization reaction system was hydrolyzed under alkaline conditions to analyze the contents of diglycolic acid, methoxy acetic acid and oxalic acid present therein. As a result, the respective contents were found to be 0 mole, 0 mole and 0.33 mole. The amount of carboxyl groups in these organic acids totaled 0.66 mole. The amount of the compound having an alcoholic hydroxyl group, added at the initial stage and the subsequent stages, was 102 grams for PEG#300, and the amount of the alcoholic hydroxyl groups totaled 0.68 mole.

Example 3

The experimentation of repetition of depolymerization reactions was initiated as in example 1. After the 10th depolymerization reaction was finished, the glycolic acid oligomer to be added was changed to glycolic acid oligomer (c) obtained in synthesis example 3. At the 11th and subsequent cycles, the depolymerization reactions were successively carried out with the addition of 60 grams of glycolic acid oligomer (c) and 150 grams of TEGDME. Until the 25th depolymerization reaction, there was no drop of the distillation rate of glycolide; the depolymerization reactions could be carried out stably at 11 to 12 grams/hour.

Upon the completion of the 25th reaction, the feed of glycolic acid oligomer added up to 1,540 grams. The depolymerization reaction system was hydrolyzed under alkaline conditions to analyze the contents of diglycolic acid, methoxy acetic acid and oxalic acid present therein. As a result, the respective contents were found to be 0.26 mole, 0.13 mole and 0 mole. The amount of carboxyl groups in these organic acids totaled 0.65 mole. The amount of PEG#300 added at the initial stage was 42 grams, and the amount of lauryl triethylene glycol contained as co-condensed in glycolic acid oligomer (c) was 128 grams. The amount of the respective alcoholic hydroxyl groups totaled 0.68 mole.

Example 4

A 500-ml flask was charged with 100 grams of glycolic acid oligomer (c) obtained in synthesis example 3 and 200 grams of TEGDME acting as the polar organic solvent. The flask was heated up to 260° C. while the inside pressure was lowered to 8.0 kPa. Glycolic acid oligomer (c) was put in a dissolved state. A distilled-out solution was cooled with ice water for entrapment.

After a five-hour reaction, the amount of the distilled-out solution was 268 grams. From this solution, 0.59 grams of glycolide and 150 grams of TEGDME were recovered. With 60 grams of glycolic acid oligomer (c) and 150 grams of TEGDME added to the reaction solution remaining in the flask, the depolymerization reaction was carried out under the same conditions as mentioned above. In this way, the depolymerization reaction was repetitively carried out with the addition of glycolic acid oligomer (c) in the weight corresponding to the amount of glycolide obtained in the distilled-out solution and TEGDME in the same amount as that of TEGDME in the distilled-out solution. Until the 25th depolymerization reaction, there was no drop of the distillation rate of glycolide; the distillation rate of glycolide was kept stable at 11 to 12 grams/hour, indicating that the stable yet efficient depolymerization reactions could be carried out over an extended period.

Upon the completion of the 25th reaction, the feed of glycolic acid oligomer added up to 1,540 grams. The depolymerization reaction system was hydrolyzed under alkaline conditions to analyze the contents of diglycolic acid, methoxy acetic acid and oxalic acid present therein. As a result, the respective contents were found to be 0.26 mole, 0.13 mole and 0 mole. The amount of carboxyl groups in these organic acids totaled 0.65 mole. The amount of lauryl triethylene glycol contained as co-condensed in glycolic acid oligomer (c) was 220 grams, and the amount of alcoholic hydroxyl groups was 0.69 mole.

Comparative Example 1

A 500-ml flask was charged with 100 grams of glycolic acid oligomer (a) obtained in synthesis example 1, 200 grams of TEGDME acting as the polar organic solvent and 42 grams (corresponding to 0.28 mole of alcoholic hydroxyl group) of PEG#300 having an average molecular weight of 300 and a boiling point of 410 to 470° C. The flask was heated up to 260° C. while the inside pressure was lowered to 8.0 kPa. Glycolic acid oligomer (a) was put in a dissolved state, and the distilled-out solution was cooled with ice water for entrapment.

After a five-hour reaction, the amount of the distilled-out solution was 210 grams. From this solution, 58 grams of glycolide and 150 grams of TEGDME were recovered. The distillation rate of glycolide was 11 to 12 grams/hour. With 60 grams of glycolic acid oligomer (a) and 150 grams of TEGDME added to the reaction solution remaining in the flask, the depolymerization reaction was carried out under the same conditions as mentioned above.

In this way, the depolymerization reaction was repetitively carried out with the addition of glycolic acid oligomer (a) in the weight corresponding to the amount of glycolide obtained in the distilled-out solution and TEGDME in the same amount as that of TEGDME in the distilled-out solution. The depolymerization reaction was repeated ten times. The feed of glycolic acid oligomer (a) added up to 640 grams. At this time, the distillation rate of glycolide decreased down to 8 to 9 grams/hour. Then, the 11th depolymerization reaction was carried out with the addition of 60 grams of glycolic acid oligomer (a) and 150 grams of TEGDME. Consequently, the distillation rate of glycolide decreased further. Likewise, the 12th to 15th depolymerization reactions were successively carried out with the addition of 60 grams of glycolic acid oligomer (a) and 150 grams of TEGDME. However, as the number of repetition increased, the distillation rate of glycolide became even much lower. At the 15th depolymerization reaction, the distillation rate of glycolide jumped down to 3 to 4 grams/hour.

Upon the completion of the 15th reaction, the feed of glycolic acid oligomer (a) added up to 940 grams. The depolymerization reaction system was hydrolyzed under alkaline conditions to analyze the contents of diglycolic acid, methoxy acetic acid and oxalic acid present therein. As a result, the respective contents were found to be 0.16 mole, 0.08 mole and 0 mole. The amount of carboxyl groups in these organic acids totaled 0.40 mole. The amount of the compound having an alcoholic hydroxyl group, added at the initial stage, was 42 grams for PEG#300, and the amount of the alcoholic hydroxyl groups totaled 0.28 mole.

INDUSTRIAL APPLICABILITY

The present invention provides a process for producing glycolide by depolymerization by heating of glycolic acid oligomers wherein, by imparting long-term stability to a depolymerization reaction system containing a glycolic acid oligomer, depolymerization reactions can be run stably yet with efficiency, even when the depolymerization reactions are carried out over an extended period.

The present invention also provides a unheard-of glycolic acid oligomer capable of reducing or substantially eliminating adverse influences ascribable to impurities contained in glycolic acid that is the raw material for glycolic acid oligomers, so that depolymerization reactions can be carried out stably yet with efficiency, even when they are run continuously or repeatedly over an extended period.

The invention claimed is:

1. A glycolide production process including a step of depolymerization by heating of a glycolic acid oligomer, wherein:

a depolymerization reaction is carried out through the following steps (i) to (iv):

step (i) of heating a depolymerization reaction system comprising a glycolic acid oligomer plus a polar organic solvent to depolymerize the glycolic acid oligomer into glycolide in a reaction vessel, step (ii) of distilling the glycolide formed by de-polymerization and the polar organic solvent out of the depolymerization reaction system, step (iii) of recovering the glycolide from distillates obtained by distillation, and step (iv) of charging the glycolic acid oligomer and the polar organic solvent in fresh amounts that make up for the amount of distillates, continuously or intermittently into the depolymerization reaction system comprising the glycolic acid oligomer and the polar organic solvent remaining in the reaction vessel, in which:

(v) during the depolymerization reaction, in order to reduce a decrease in the formation rate of glycolide, a compound (A) having an alcoholic hydroxyl group is permitted to exist in the de-polymerization reaction system, provided that the amount of the compound (A) in the depolymenzation reaction system is controlled such that the alcoholic hydroxyl group amount of said compound (A) is kept at 0.5 equivalent or greater with respect to the total carboxyl group amount of an organic acid (B) comprising diglycolic acid, methoxy acetic acid and oxalic acid formed upon hydrolysis of the depolymerization reaction system under alkaline conditions, wherein the amount of compound (A) in the depolymerization reaction system is controlled at said amount of 0.5 equivalent or greater by a) adding the compound (A) into the reaction vessel in the step (i), and then adding the compound (A) continuously or intermittently into the depolymerization reaction system in the step iv) before the total carboxyl group amount of the organic acid (B) in the depolymerization reaction system reaches the said equivalent or greater with respect to the alcoholic hydroxyl group amount of the originally added compound (A); or b) using as the glycolic acid oligomer a alycolic acid oligomer obtained by condensation of glycolic acid in the presence of the compound (A); and wherein the depolymerization reaction is carried out continuously or repeatedly in said depolymerization reaction system.

2. The production process according to claim 1, wherein during the depolymerization reaction, the amount in the depolymerization reaction system of the compound (A) having an alcoholic hydroxyl group is controlled such that the alcoholic hydroxyl group amount of said compound (A) is kept at 0.9 equivalent or greater with respect to the total carboxyl group amount of said organic acid (B).

3. The production process according to claim 1, wherein the compound (A) having an alcoholic hydroxyl group has a boiling point of 190° C. or higher.

4. The production process according to claim 1, wherein the compound (A) having an alcoholic hydroxyl group is added into the depolymerization reaction system, whereby, during the depolymerization reaction, the amount of said compound (A) in the depolymerization reaction system is controlled such that the alcoholic hydroxyl group amount of said compound (A) is kept at 0.5 equivalent or greater with respect to the total carboxyl group amount of said organic acid (B).

5. The production process according to claim 1, wherein the glycolic acid oligomer obtained by condensation of glycolic acid in the presence of the compound (A) having an alcoholic hydroxyl group is used as the glycolic acid oligomer, whereby, during the depolymerization reaction, the amount of said compound (A) in the depolymerization reaction system is controlled such that the alcoholic hydroxyl group amount of said compound (A) is kept at 0.5 equivalent or greater with respect to the total carboxyl group amount of said organic acid (B).

6. The production process according to claim 5, wherein the compound (A) having an alcoholic hydroxyl group has a boiling point of 190° C. or higher.

7. The production process according to claim 1, wherein the compound (A) having an alcoholic hydroxyl group is at least one compound selected from the group consisting of an alkylene diol, a polyalkylene glycol and a polyalkylene glycol monoether.

8. The production process according to claim 1, wherein at said step (i) the depolymerization reaction system comprising the glycolic acid oligomer and the polar organic solvent is heated to depolymerize the glycolic acid oligomer into glycolide, said step (ii) the glycolide formed by depolymerization and the polar organic solvent are distilled out of the depolymerization reaction system, and at said step (iii) the glycolide is separated and recovered from distillates obtained by distillation.

9. The production process according to claim 8, wherein at said step (i) the depolymerization reaction system comprises a mixture containing the glycolic acid oligomer and the polar organic solvent, the polar organic solvent has a boiling point in the range of 230 to 450° C. the depolyermization reaction system is heated under normal pressure or reduced pressure in such a state that the proportion of a remaining glycolic acid oligomer melt phase in said mixture is 0.5 or less, and heating is continued in that state to depolymerize the glycolic acid oligomer into glycolide.

10. The production process according to claim 9, wherein the polar organic solvent has a molecular weight in the range of 150 to 450.

11. The production process according to claim 9, wherein the polar organic solvent is a polyalkylene glycol diether.

12. The production process according to claim 9, wherein said mixture further contains the compound (A) having an alcoholic hydroxyl group.

13. The production process according to claim 1, wherein the compound (A) having an alcoholic hydroxyl group is continuously or intermittently charged to the depolymerization reaction system, whereby, during the depolymerization reaction, the amount of said compound (A) in the depolymerization reaction system is controlled such that the alcoholic hydroxyl group amount of said compound (A) is kept at 0.5 equivalent or greater with respect to the total carboxyl group amount of said organic acid (B).

14. The production process according to claim 1, wherein the glycolic acid oligomer is obtained by condensation of glycolic acid in the presence of the compound (A) having an alcoholic hydroxyl group and is continuously or intermittently charged into the depolymerization reaction system, whereby, during the depolymerization reaction, the amount of said compound (A) in the depolymerization reaction system is controlled such that the alcoholic hydroxyl group amount of said compound (A) is kept at 0.5 equivalent or greater with respect to the total carboxyl group amount of said organic acid (B).

15. A glycolic acid oligomer for the production of glycolide, wherein the glycolic acid oligomer is obtained by condensation of glycolic acid in the presence of a compound (A) having an alcoholic hydroxyl group and a boiling point of 190° C. or higher, wherein an amount of the alcoholic hydroxyl group of said compound (A) is in the range of 0.5 to 1.5 equivalents with respect to the total carboxyl group amount of an organic acid (B) comprising diglycolic acid, methoxy acetic acid and oxalic acid formed upon the hydrolysis under alkaline conditions of the glycolic acid oligomer obtained by condensation, and wherein the glycolic acid oligomer has a melting point of 140° C. or higher.

16. The glycolic acid oligomer for the production of glycolide according to claim 15, wherein the compound (A) having an alcoholic hydroxyl group is at least one compound selected from the group consisting of an alkylene diol, a polyalkylene glycol and a polyalkylene glycol monoether.

17. The glycolic acid oligomer for the production of glycolide according to claim 15, wherein the glycolic acid oligomer has a melting point of 160° C. higher.

18. The glycolic acid oligomer for the production of glycolide according to claim 15, wherein the glycolic acid has a melting point of 180° C. or higher.

* * * * *

UNITED STATES PATENT AND TRADEMARK OFFICE
CERTIFICATE OF CORRECTION

| | |
|---|---|
| PATENT NO. | : 7,235,673 B2 |
| APPLICATION NO. | : 10/472719 |
| DATED | : June 26, 2007 |
| INVENTOR(S) | : Kazuyuki Yamane et al. |

Page 1 of 1

It is certified that error appears in the above-identified patent and that said Letters Patent is hereby corrected as shown below:

Claim 1, column 20, line 39, change "alycolic" to --glycolic--.

Claim 13, column 22, line 1, change "to" to --into--.

Signed and Sealed this

Thirtieth Day of October, 2007

JON W. DUDAS
*Director of the United States Patent and Trademark Office*